(12) United States Patent
Smoragiewicz et al.

(10) Patent No.: US 8,926,960 B2
(45) Date of Patent: Jan. 6, 2015

(54) **GROWTH INHIBITION AND ELIMINATION OF METHICILLIN-RESISTANT *STAPHYLOCOCCUS AUREUS* BY LACTIC ACID BACTERIA**

(75) Inventors: Wanda Smoragiewicz, Montreal (CA); Barbara Karska-Wysocki, Montreal (CA); Antoni Wysocki, legal representative, Montreal (CA); Mari Bazo, Montreal (CA); Marcia Ruiz, Dollard-des-Ormeaux (CA); François-Marie Luquet, Paris (FR)

(73) Assignee: Bio-K Plus International Inc., Laval, Quebec (CA)

( * ) Notice: Subject to any disclaimer, the term of this patent is extended or adjusted under 35 U.S.C. 154(b) by 376 days.

(21) Appl. No.: 12/814,661

(22) Filed: Jun. 14, 2010

(65) Prior Publication Data

US 2011/0195057 A1    Aug. 11, 2011

Related U.S. Application Data

(63) Continuation of application No. 12/520,215, filed as application No. PCT/CA2007/002348 on Dec. 21, 2007, now abandoned.

(60) Provisional application No. 60/876,460, filed on Dec. 22, 2006.

(51) Int. Cl.
| | | |
|---|---|---|
| *C12P 1/04* | (2006.01) | |
| *C12N 1/20* | (2006.01) | |
| *C12R 1/245* | (2006.01) | |
| *C12R 1/23* | (2006.01) | |
| *A01N 63/00* | (2006.01) | |
| *A23C 9/123* | (2006.01) | |
| *A23C 11/10* | (2006.01) | |
| *A23L 1/30* | (2006.01) | |
| *A61K 35/74* | (2006.01) | |

(52) U.S. Cl.
CPC . *C12N 1/20* (2013.01); *C12R 1/245* (2013.01); *C12R 1/23* (2013.01); *A01N 63/00* (2013.01); *A23C 9/123* (2013.01); *A23C 11/106* (2013.01); *A23L 1/3014* (2013.01); *A23Y 2220/17* (2013.01); *A61K 35/747* (2013.01)
USPC ........................................ 424/93.45; 435/170

(58) Field of Classification Search
CPC ................................. C12R 1/23; C12R 1/245
USPC ........................................ 424/93.45; 435/170
See application file for complete search history.

(56) References Cited

U.S. PATENT DOCUMENTS 6,607,905 B1    8/2003    Luquet

FOREIGN PATENT DOCUMENTS

| EP | 1338205 A1 | 8/2003 |
|---|---|---|
| WO | WO98/35014 A2 | 8/1998 |

OTHER PUBLICATIONS

Nawaz Syed Kashif, et al.: Screening for anti-methicillin resistant *Staphylococcus aureus* (MRSA) bacteriocin producing bacteria Feb. 4, 2009 African Journal of Biotechnology, vol. 8, pp. 365-368.
Schellenberg, et al.: "A rapid method combining immunofluorescence and flow cytometry for improved understanding of competitive interactions between lactic acid bacteria (LAB) and methicillin-resistant *S. aureus* (MRSA) in mixed culture" Journal of Microbiological Methods, Elsevier, Amsterdam (Apr. 1, 2006), vol. 65, No. 1, pp. 1-9.
Sabine D.B.: "An antibiotic-like effect of *Lactobacillus acidophilus*" Nature (1963), vol. 199, No. 4895, p. 811.
Abo-Amer A. E.: "Chromosomal genes-mediated inhibition of intestinal and foodborne pathogens by *Lactobacillus acidophilus* AA11" Revista Latino America (2006) vol. 48, No. 1, pp. 24-30.
Vincent J.G., et al.: "Antibacterial activity associated with *Lactobacillus acidophilus*" J. Bacteriol. (1959), vol. 78, pp. 477-484.
Voravuthikunchal S.P., et al.: "Antagonistic activity against pathogenic bacteria by human vaginal lactobacilli" Anaerobe (2006) vol. 12, pp. 221-226.
Otero M.C., et al.: "Inhibition of *Staphylococcus aureus* by H2O2-producing *Lactobacillus gasseri* isolated from vaginal tract of cattle" Anim. Reprod. Sci (2006), vol. 96, pp. 35-46.
Millette M., et al.: "In vitro growth control of selected pathogens by *Lactobacillus acidophilus*-and *Lactobacillus casei*-fermented milk" Lett. Appl. Microbiol., (2007) vol. 44, No. 3, pp. 314-319.
Alvarez-Olmos, et al.: "Probiotic agents and infectious diseases: a modern perspective on a traditional therapy" Clin Infect Dis. (2001), vol. 32 (11): 1567-76.
D'Souza, et al.: "Probiotics in prevention of antibiotic associated diarrhoea: meta-analysis" BMJ (2002), vol. 324 (7350): 1361.
Jacobsen, et al.: "Screening of probiotic activities of forty-seven strains of *Lactobacillus* spp. by in vitro techniques and evaluation of the colonization ability of five selected strains in humans" Appl Environ Microbiol. (1999), vol. 65 (11):4949-56.
Lu, et al.: "Pathologic and physiologic interactions of bacteria with the gastrointestinal epithelium" Am J Clin Nutr. (2001), vol. 73(6):1124s-1130s.

(Continued)

*Primary Examiner* — Ruth Davis
(74) *Attorney, Agent, or Firm* — Dentons US LLP

(57) ABSTRACT

The present invention relates to methicillin-resistant *Staphylococcus aureus* growth inhibition by lactic acid bacterium strains. More specifically it is directed to the use of lactic acid bacterium strains, compositions comprising lactic acid bacterium strains, methods of use and kits thereof to inhibit the growth of methicillin-resistant *Staphylococcus aureus*. This invention more specifically relates to the inhibitory effect of lactic acid bacterium strains *Lactobacillus acidophilus* and *Lactobacillus caseion* methicillin-resistant *Staphylococcus aureus*.

7 Claims, 2 Drawing Sheets

(56) References Cited

OTHER PUBLICATIONS

Martins, et al.: "Methicillin resistance in *Staphylococcus aureus* and coagulase-negative staphylococci: epidemiological and molecular aspects" Microbiol. Immunol. (2007), vol. 51 No. 9, pp. 787-795.

Mathur S, et al.: "Antibiotic resistance in food lactic acid bacteria—a review" Int. Journal of Food Microbiology (2005), vol. 105, 281-295.

Report of an expert meeting "Current level of consensus on probiotic science", London, Nov. 23, 2009 (8 pages).

Report of a Joint FAO/WHO Working Group on Drafting Guidelines for the Evaluation of Probiotics in Food "Guidelines for the Evaluation of Probiotics in Food", London Ontario, Canada, Apr. 30 and May 1, 2002 (11 pages).

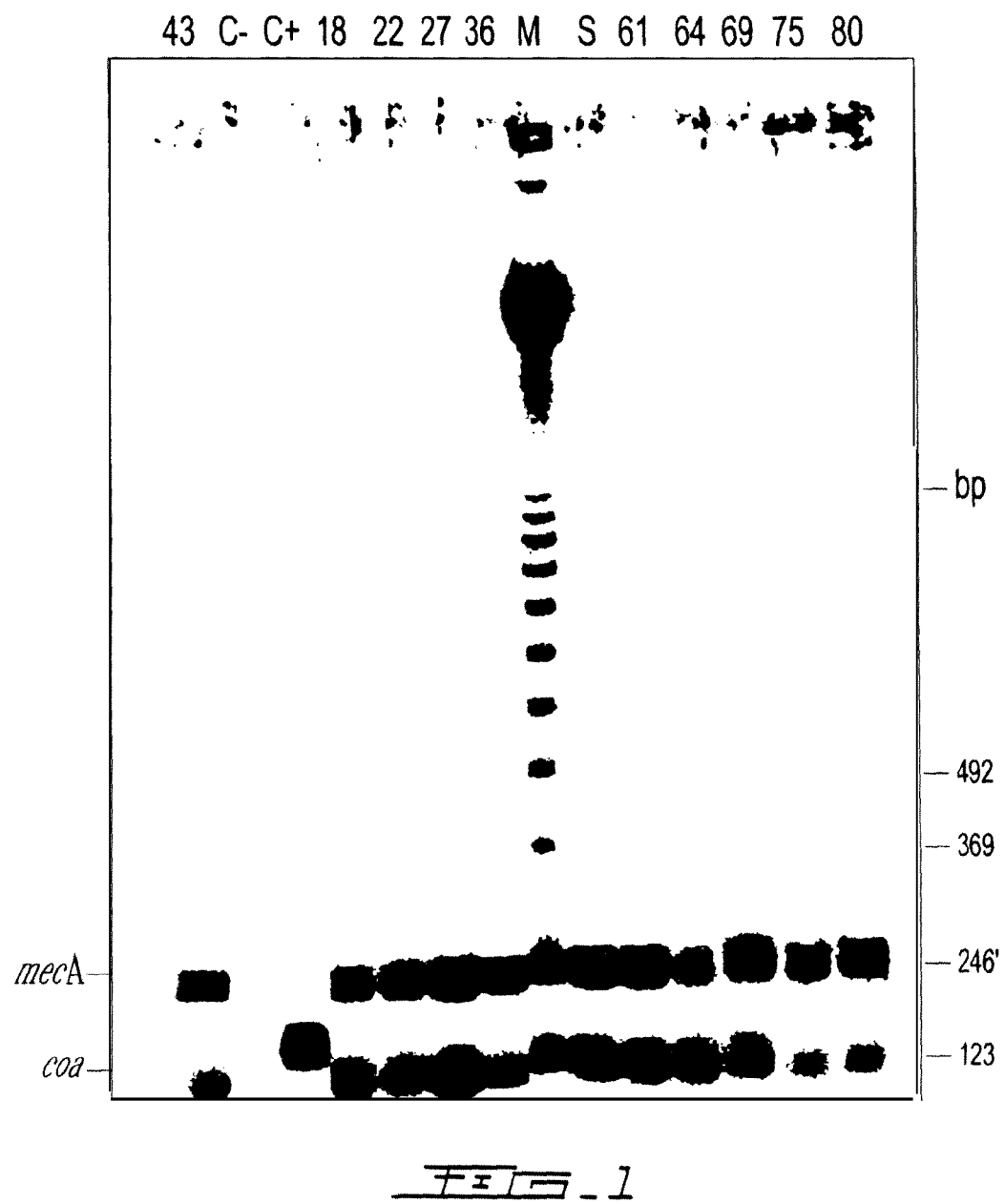
FIG_1

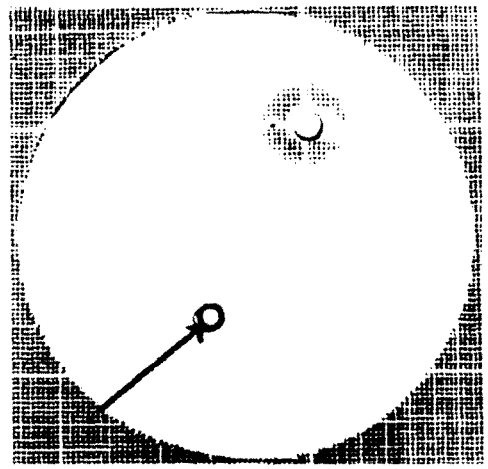
FIG._2A
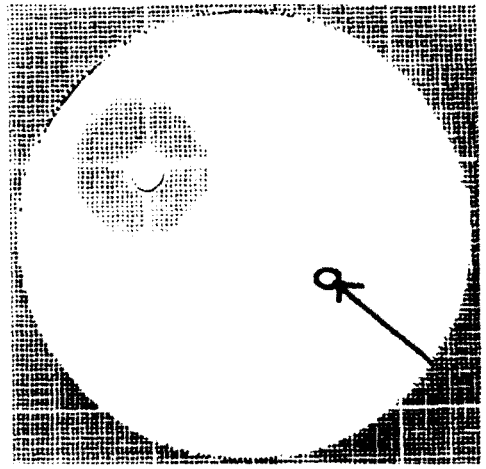
FIG._2B
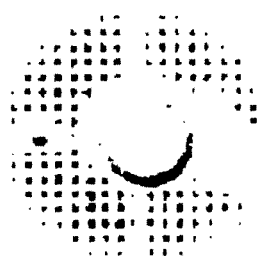
FIG._3A
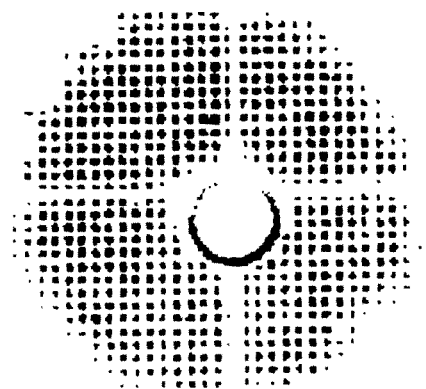
FIG._3B

US 8,926,960 B2

GROWTH INHIBITION AND ELIMINATION OF METHICILLIN-RESISTANT *STAPHYLOCOCCUS AUREUS* BY LACTIC ACID BACTERIA

RELATED APPLICATIONS

The present application is a continuation of U.S. application Ser. No. 12/520,215, filed Jun. 19, 2009, which is a U.S. National Phase Application of International Application PCT/CA2007/002348, filed Dec. 21, 2007, which claims the benefit of U.S. Application No. 60/876,460, filed Dec. 22, 2006, all of which are herein incorporated by reference in their entirety.

FIELD OF INVENTION

The present invention relates to methicillin-resistant *Staphylococcus aureus* growth inhibition by lactic acid bacteria.

BACKGROUND OF THE INVENTION

Lactic acid bacteria (LAB) are Gram-positive bacteria that produce lactic acid by the fermentation of glucose. Lactic acid bacteria have been widely used in various fermented food products around the world for many centuries and have been shown to exhibit various beneficial biological functions. Some lactic acid bacteria are also referred to as probiotics. According to the World Health Organization, the term "probiotics" describes live microorganisms which confer a health benefit to a host. The most frequently used species are *Lactobacillus* spp., *Bifidobaterium* spp. and *Saccharomyces* spp. A number of mechanisms of action have been proposed to explain the efficacy of probiotics. These mechanisms include production of antimicrobial substances, competition for gastro-intestinal colonization as well as for available nutrients, production of antimicrobial bacteriocins, immunomodulation and promotion of lactose digestion (Lu et al., 2001; D'Souza et al., 2002; Alvarez-Olmos et al., 2001).

Antibiotics have substantially decreased morbidity and mortality from bacterial infections in the $20^{th}$ century. However, microorganisms are showing more and more resistance to existing antibiotics. This antibiotic resistance phenomenon is a serious threat to public health. Probiotics may act as biotherapeutic agents and help solve public health issues pertaining to multidrug resistance. Methicillin resistant *Staphylococcus aureus* (MRSA) is a specific strain of bacteria that shows resistance to many antibiotics including methicillin. MRSA infections are typically acquired in healthcare (nosocomial infections) and community settings. Although *Staphylococcus aureus* strains usually utilize three penicillin-binding proteins (PBP) in the synthesis of their cell wall, those that are resistant to methicillin (MRSA) possess a supplementary PBP, PBP2a, encoded by the mecA gene which allows cells to grow in the presence of methicillin, oxacillin and other beta-lactam antibiotics (Martins et al., 2007).

It is estimated that more than 90% of *Staphylococcus aureus* infections are resistant to methicillin and other antibiotics (Mathur and Singh, 2005). The lack of efficacy of various antibiotics and the increasing prevalence of MRSA has become a major public health issue and resistance of Staphylococci to methicillin is a problem of global proportions. There is a clear need for new antibacterial agents to control methicillin-resistant *Staphylococcus aureus*. Such agents would provide significant therapeutic value for the prevention, reduction and/or treatment of MRSA infections. The present invention seeks to meet this and other needs.

The present description refers to a number of documents, the content of which is herein incorporated by reference in their entirety.

SUMMARY OF THE INVENTION

In one aspect thereof, the present invention relates to the use of at least one lactic acid bacterium strain for inhibiting (reducing, decreasing, lowering, impairing, eliminating) the growth of a methicillin-resistant *Staphylococcus aureus* and/or for treating a methicillin-resistant *Staphylococcus aureus* infection.

In a second aspect thereof, the present invention relates to a method for inhibiting the growth of a methicillin-resistant *Staphylococcus aureus* and/or treating a methicillin-resistant *Staphylococcus aureus* infection. The method may comprise administering an effective amount of at least one lactic acid bacterium strain to a subject in need thereof.

In a third aspect thereof, the present invention relates to a kit for inhibiting the growth of a methicillin-resistant *Staphylococcus aureus* and/or treating a methicillin-resistant *Staphylococcus aureus* infection. The kit may comprise at least one container containing at least one lactic acid bacterium strain.

In a fourth aspect thereof, the present invention relates to a composition for use in inhibiting the growth of a methicillin-resistant *Staphylococcus aureus*. The composition may comprise an effective amount of at least one lactic acid bacterium strain and a pharmaceutically acceptable vehicle.

In a fifth aspect thereof, the present invention relates to the use of a composition comprising an effective amount of at least one lactic acid bacterium strain and a pharmaceutically acceptable vehicle for inhibiting the growth of a methicillin-resistant *Staphylococcus aureus* and/or for treating a methicillin-resistant *Staphylococcus aureus* infection.

BRIEF DESCRIPTION OF DRAWINGS

In drawings which illustrate non-limitative exemplary embodiments of the present invention, FIG. 1 shows the detection of the coa (117 bp) and mecA (214 bp) genes in all tested clinical isolates and control *S. aureus* strain, C+ represent a PCR positive control, C− represent a PCR negative control, M represent a molecular weight marker and S represents the ATCC Standard MRSA strain ATCC 43300;

FIG. 2 shows the antibacterial activity of *Lactobacillus casei* on MRSA clinical isolate #43 (panel A) or MRSA ATCC Standard 43300 (panel B);

FIG. 3 shows the antibacterial activity of *Lactobacillus casei* (panel A) and *Lactobacillus acidophilus* (panel B) on MRSA clinical isolate #43.

DETAILED DESCRIPTION OF THE INVENTION

In order to provide a clear and consistent understanding of the terms used in the present disclosure, a number of definitions are provided below. Moreover, unless defined otherwise, all technical and scientific terms as used herein have the same meaning as commonly understood to one of ordinary skill in the art to which this invention pertains.

As used in the specification and claim(s), the words 'comprising' (and any form of comprising, such as 'comprise' and 'comprises'), 'having' (and any form of having, such as 'have' and 'has'), 'including' (and any form of including, such as 'include' and 'includes') or 'containing' (and any form of containing, such as 'contain' and 'contains'), are inclusive or open-ended and do not exclude additional, unrecited elements.

In one aspect thereof, the present invention relates to the use of at least one lactic acid bacterium strain for inhibiting (reducing, decreasing, lowering, impairing) the growth of a methicillin-resistant *Staphylococcus aureus* and/or for treating a methicillin-resistant *Staphylococcus aureus* infection.

In the present invention, a lactic acid bacterium strain may be a *Lactobacillus*. In a further embodiment, a lactic acid bacterium strain may be *Lactobacillus acidophilus, Lactobacillus casei* and/or a mixture thereof. Any strains of *Lactobacillus acidophilus* or *Lactobacillus casei* may be used as long as they do not show deleterious effects. These strains may be of commercial origin and may be purchased from manufacturers of lactic ferments. In a further embodiment, a *Lactobacillus acidophilus* strain may comprise strain I-1492 deposited on Nov. 15, 1994 at the Collection Nationale de Cultures de Microorganismes (CNCM; Institut Pasteur, 28 Rue du Docteur Roux, F-75724, Paris, CEDEX 15) according to the provisions of the Budapest Treaty.

By "mixture" it is meant the combination of lactic acid bacterium strains in any given proportions. The mixture of the present invention may comprise *L. acidophilus* I-1492 strain. For example such mixture may comprise about 95% of *L. acidophilus* strain I-1492 and/or about 5% of *L. casei*. In another example, a mixture may comprise for example and without limitation, from about 25% to about 100% (25% to 75%, 33% to 75%, 50% to 75%, 65% to 75%, 75% to 99% of *L. acidophilus*—such as strain I-1492). In an embodiment of the invention, the proportion of *L. acidophilus* is higher than 60%. The present invention relates to, and explicitly incorporates herein, each and every specific member and combination of lactic acid bacterium strain proportions whatsoever.

It is to be understood herein that by "inhibiting" it is meant a process by which the microorganisms (methicillin resistant *Staphylococcus aureus*) and/or the infections (for example, a methicillin resistant *Staphylococcus aureus* infection) may be reduced, delayed, prevented and/or impaired. Such inhibition may occur at any time following contact of a lactic acid bacterium strain with MRSA. For example, inhibition may occur from about 0.1 to about 72 h after contact. The present invention relates to, and explicitly incorporates herein, each and every specific member and combination of contact time sub-ranges whatsoever. Inhibition of the (growth of) microorganisms (MRSA) may be partial and/or complete (eradication). For example, inhibition may be at least 50% inhibition (or at least 60%, or at least 65%, or at least 70%, or at least 75%, or at least 80%, or at least 85%, or at least 90%, or at least 95%, or at least 99%). In an embodiment of the present invention, the growth of MRSA is inhibited at least by 99% (complete inhibition; eradication). The present invention relates to, and explicitly incorporates herein, each and every specific member and combination of inhibition sub-ranges whatsoever. It is also to be understood herein that by "treating" it is meant a process by which the symptoms of infections (for example, a methicillin-resistant *Staphylococcus aureus* infection; an infection with one and/or more than one strain of methicillin-resistant *Staphylococcus aureus*) may not worsen, may remain stable, may be reduced (reducing a MRSA infection) and/or may be completely eliminated (eliminating and/or eradicating a MRSA infection).

In a second aspect thereof, the present invention relates to a method for inhibiting the growth of a methicillin-resistant *Staphylococcus aureus* and/or for treating a methicillin-resistant *Staphylococcus aureus* infection. The method may comprise administering an effective amount of at least one lactic acid bacterium strain to a subject in need thereof.

A subject in need thereof may be a mammal (such as a human) infected with, suspected to be infected with and/or at risk of being infected with a MRSA. A subject at risk of being infected with a MRSA may include family members or any subject (mammal; human) which have been in close proximity to an infected subject (mammal; human). The quantity and/or concentration of at least one lactic acid bacterium strain which may be administered to a subject in need thereof may be an "effective amount". An effective amount of a lactic acid bacterium strain is the necessary quantity to obtain positive results without causing excessively negative effects in the subject to which the lactic acid bacterium strain (or a composition thereof) is administered. An effective amount of a lactic acid bacterium strain to inhibit the growth of a MRSA is a quantity which is sufficient to inhibit in any manner the growth of MRSA either totally or partially. An effective amount may also encompass either "therapeutically effective amount" and/or "prophylactically effective amount". A "therapeutically effective amount" refers to an amount effective, at dosages and for periods of time necessary, to achieve the desired therapeutic result, such as a reduction in disease progression (for example a MRSA infection) and/or alleviation of the symptoms associated with a disease. A therapeutically effective amount may vary according to factors such as the disease state, age, sex, and weight of a subject, and the ability of an agent to elicit a desired response in a subject. Dosage regimens may be adjusted to provide the optimum therapeutic response. A therapeutically effective amount is also one in which any toxic or detrimental effects of the agent are outweighed by the therapeutically beneficial effects. A "prophylactically effective amount" refers to an amount effective, at dosages and for periods of time necessary, to achieve the desired prophylactic result, such as preventing and/or reducing the rate of disease onset or progression (for example a MRSA infection). A prophylactically effective amount may be determined as described above for the therapeutically effective amount. For any particular subject, specific dosage regimens may be adjusted over time according to a subject's need and the professional judgment of the person administering of the compositions.

An effective amount may be administered (to a subject in need thereof) in one or more administrations, according to a regimen. The privileged method of administration and the quantity that may preferably be administered may be a function of many factors. Among the factors that may influence this choice are, for example, the exact nature of the ingredients, active or not, entering in a composition and/or the condition, the age and the weight of a subject in need thereof. In an embodiment of the present invention, administration may be oral administration. In another embodiment of the present invention, administration may be suppository (rectal) administration. As a result of administration, lactic acid bacteria may be found in the digestive tract of a subject.

In a third aspect thereof, the present invention relates to a kit for inhibiting the growth of a methicillin-resistant *Staphylococcus aureus* and/or for treating a methicillin-resistant *Staphylococcus aureus* infection. The kit may comprise at least one (one or more than one) container containing at least one lactic acid bacterium strain. The kit of the present invention may additionally include, if desired, one or many conventional pharmaceutical components, for example, containers that may comprise one or many pharmaceutically acceptable vehicles, or any other additional containers that may be evident to a person skilled in the art. A kit according to the present invention may advantageously include instructions in the form of a pamphlet or of any other support, indicating the quantities of the lactic acid bacterium strain and/or compositions to be administered, the instructions for the administration and/or the instructions to mix given components.

In a fourth aspect thereof, the present invention relates to a composition for use in inhibiting the growth of a methicillin-resistant *Staphylococcus aureus*. The composition may comprise an effective amount of at least one lactic acid bacterium strain and a pharmaceutically acceptable vehicle.

A "composition" according to the present invention may be in a solid and/or a liquid form, usual for pharmaceutical and/or nutritional administration. More particularly, a composition according to the present invention may be presented in a variety of ingestible forms, for example, milk, yogurt, curd, fermented milks, milk-based fermented products, soy-based fermented products, fermented cereal-based products, milk-based powders and/or infant formulae. The composition may be administered in the form of food and/or food supplements. Such foods may be protein concentrates such as those used in hospitals. In case of a pharmaceutical preparation, the product may be prepared in forms of capsules, tablets, liquid bacterial suspensions, dried oral supplements, wet oral supplements, dry tube feeding, wet tube feeding, etc. In an embodiment of the invention, the composition may be obtained by fermenting lactic acid bacteria in a milk-based medium. In a further exemplary embodiment of this invention, the composition comprises Bio-K Plus™ products. Bio-K Plus™ products are lactic ferment products readily available on the market and sold by the company Bio-K Plus™ International Inc. For this purpose, the following process may be used.

Firstly, *Lactobacillus acidophilus* (including strain I-1492) and *Lactobacillus casei* strains are incubated in a MRS type fermentation medium according to a standard program comprising several steps. The recombined lacteal base, which is partially lactose-free and degassed, is pasteurized for 1.5 minutes at 95° C. and inoculated at 10%. Finally, it is incubated according to the following program:

1) the I-1492 strain: 2 hours at 37° C.
2) the acidophilus strain: 2 hours at 37° C. and
3) the casei strain: 1 hour at 37° C.

The product is then co-fermented in an anaerobic atmosphere and medium for 15 hours at 37° C. (degassing under $CO_2$).

Although total amino acid content in such composition is similar to milk, free amino acids are significantly higher. The level of peptides comprised in the composition of the invention, having a molecular weight between 1000 and 5000 Da is around 30% and the level of small peptides having less than 10 residues is approximately 15%. It is known that such levels of peptides fortify, in a surprising way, the immune and digestive systems.

By "pharmaceutically acceptable vehicle" it is meant a vehicle that may be administered to a subject, in particular to a human, with little or no negative (toxic) side effects. Such a vehicle may be used for different functions. For example, it may be used as a preservation, solubilizing, stabilizing, emulsifying, softening, coloring, odoring and/or as an antioxidant agent. Pharmaceutically acceptable vehicle of the invention encompass nutritionally acceptable vehicles, namely, any liquid and/or solid form of nourishment that an organism (such as a mammal; in particular a human) may assimilate.

The present invention also relates to the use of a composition comprising an effective amount of at least one lactic acid bacterium strain and a pharmaceutically acceptable vehicle in the manufacture of a medicament for inhibiting the growth of a methicillin-resistant *Staphylococcus aureus* and/or for treating a methicillin-resistant *Staphylococcus aureus* infection.

The following examples illustrate potential applications of the invention and are not intended to limit its scope. Modifications and variations may be made therein without departing from the spirit and scope of the invention.

Example 1

Isolation and Characterization of Methicillin Resistant *Staphylococcus Aureus* (MRSA) Clinical Strains Ten clinical methicillin-resistant *S. aureus* isolates were obtained (Shabnam Y, 2002) from different clinical infections as shown in TABLE 1.

TABLE 1

MRSA CLINICAL STRAINS ISOLATION

| Clinical Isolate # | Clinical Infection Site |
|---|---|
| 18 | Nose |
| 22 | Calf wound |
| 27 | Thigh wound |
| 36 | Abdominal pus |
| 43 | Lungs |
| 61 | Vagina |
| 64 | Eye |
| 69 | Nose |
| 75 | Tongue |
| 80 | Wound pus |

The antibiotic sensitivity of all isolated strains was tested according to the standard methodology suggested by the Canadian Committee on Antibiotic Resistance (Shabnam Y, 2002). All strains were shown to be vancomycin sensitive but resistant to methicillin, oxacillin, erythromycin and cefazolin antibiotics. *Staphylococcus* species are divided into coagulase-positive Staphylococci, represented by *S. aureus*, and coagulase-negative Staphylococci which comprise different species. Methicillin resistance is encoded by the mecA gene. To confirm the clinical isolates' identity, their genomic DNA was isolated (DNA isolation kit, Roche Applied Science) following a 24 h culture in presence of oxacillin at a concentration of 8 µg/mL. Genomic DNA was tested for the presence or absence of the mecA and coa genes by PCR (Novocastra kit—primer set NCL-SA-PS, Vision BioSystems Inc.). Results are shown in FIG. 1. All isolated clinical isolates were coa and mecA positive.

Example 2

Antibacterial Activity of *L. Acidophilus* I-1492 and *L. Casei* on MRSA Clinical Isolate #43 in Mixed Liquid Cultures The biological effect of *Lactobacillus acidophilus* I-1492 and *Lactobacillus casei* on methicillin-resistant clinical isolate #43 was studied in mixed liquid cultures. The experimental protocol was as follows. A pre-culture was prepared by incubating 5000 of bacteria in 10 ml peptone milk (Sigma) at 37° C. for 24 h. The viability of monocultures over time was recorded as shown in TABLE 2 by performing continuous culture conditions. Colony forming units were measured by standard methods by counting the colonies formed on peptone milk solid media. These pre-cultures served as starting material for mixed cultures.

TABLE 2

MONOCULTURES VIABILITY AS A FUNCTION OF TIME

| INCUBATION TIME (h) | L. ACIDOPHILUS I-1492 × $10^8$ CFU/mL | L. CASEI × $10^8$ CFU/mL | MRSA #43 × $10^8$ CFU/mL |
|---|---|---|---|
| 24 | 1.29 | 3.20 | 3.76 |
| 48 | 3.54 | 2.33 | 3.80 |
| 72 | 1.34 | 2.26 | 2.30 |

Mixed cultures were prepared in liquid media by mixing 100 μl of *L. acidophilus* (1.3×10⁶ cells), 100 μl *L. casei* (3.2×10⁶ cells) and 100 μl MRSA, #43 (3.8×10⁶ cells) in 10 ml of peptone milk. The mixed cultures were grown for 24 h, 48 h and 72 h and CFU were measured using peptone milk agar or MRSA selective media (Mannitol Salt Agar-MSA). As shown in TABLE 3, after 24 h of incubation in presence of *L. casei* and *L. acidophilus*, MRSA bacteria were inhibited by more than 99% (eliminated). These results clearly show the inhibitory effect of a mixture of lactic acid bacteria (*L. acidophilus* and *L. casei*) on MRSA.

TABLE 3

VIABLE MRSA COUNT FOLLOWING MIXED CULTURES

| Incubation time (h) | Peptone Milk Media × $10^8$ CFU/mL | MSA × $10^3$ CFU/mL |
|---|---|---|
| 24 | 3.65 | 2.99 |
| 48 | 2.12 | 0 |
| 72 | 1.07 | 0 |

Example 3

Antibacterial Activity of *Lactobacillus Casei* on MRSA ATCC STD 43300 and MRSA Clinical Isolate #43

In FIG. 2, the growth inhibitory effect of *Lactobacillus casei* on either MRSA clinical isolate #43 or MRSA ATCC Standard 43300 was compared to lactic acid bacterial strain *Lactococcus lactis* ssp *cremoris* using antimicrobial susceptibility testing method (discussed in Jacobsen et al. 1999 and Schellenberg et al. 2006). The experimental protocol was as follows. 3 μl of a 24 h culture of *Lactobacillus casei* or a mixture thereof was spotted on a Petri dish containing 7 ml of Monn-Rogosa-Sharpe (MRS) agar and incubated at 37° C. for 24 h in anaerobic conditions. The following day, 2000 of a 24 h culture of methicillin-resistant *Staphylococcus aureus* clinical isolate #43 was added to a 1:1 mixture of Brain Heart Infusion (BHI) and MRS containing 0.7% agar and poured onto the previously spotted Petri dish. The Petri dish was further incubated for 24 h to 48 h under aerobic conditions. Inhibition diameters could then be calculated and Petri dish photographed to record results. Only agents inhibiting MRSA growth can form zones of inhibition around the inoculated region. *Lactobacillus casei* showed growth inhibitory effect as seen with an inhibitory zone of 2 cm (panel A) and a growth inhibitory effect on MRSA ATCC Standard 43300 as shown with an inhibitory zone of 3 cm (panel B). *Lactobacillus casei* is therefore effective at inhibiting the growth of both ATCC standard 43300 MRSA strain and a MRSA clinical isolate. In both panels, inoculation of the lactic acid bacteria *Lactococcus lactis* spp *cremoris* culture did not result in growth inhibition and no inhibitory zone was detected (FIG. 2, arrow). Thus, not all lactic acid bacteria inhibit the growth of methicillin-resistant *Staphylococcus aureus* and *L. casei* inhibits both standard and clinical MRSA.

Example 4

Antibacterial Activity of *L. Acidophilus* I-1492 and *L. Casei* on MRSA Clinical Isolate #43

The biological effect of *Lactobacillus acidophilus* and *Lactobacillus casei* on methicillin-resistant clinical isolate #43 was studied using antimicrobial susceptibility testing as described above for *L. casei*. As shown in FIG. 3, both *Lactobacillus acidophilus* and *Lactobacillus casei* inhibited MRSA clinical isolate #43 growth as shown by a 2 cm inhibition zone for *Lactobacillus casei* (panel A) and a 3 cm inhibition zone for *Lactobacillus acidophilus* (panel B). Therefore, both lactic acid bacterium strains show an inhibitory effect on MRSA growth.

Example 5

Antibacterial Activities of *Lactobacillus Casei* and *Lactobacillus Acidophilus* on Various MRSA Clinical Isolates The growth inhibitory effect of *L. casei* and *L. acidophilus* was tested on ten different clinical methicillin-resistant *Staphylococcus aureus* isolates. Three independent experiments were performed and the average (avg) inhibition diameter is shown in TABLE 4.

TABLE 4

INHIBITORY EFFECT OF *L. CASEI* OR *L. ACIDOPHILUS* ON MRSA CLINICAL ISOLATES

| | Inhibition Diameter (cm) | | | | | | | | |
|---|---|---|---|---|---|---|---|---|---|
| Clinical Isolate # | *Lactobacillus acidophilus* I-1492 | | | | *Lactobacillus casei* | | | | *Lactococcus cremoris* |
| | Exp1 | Exp2 | Exp3 | Avg | Exp1 | Exp2 | Exp3 | Avg | |
| 43 | 3 | 2.8 | 3 | 2.9 | 2 | 2.2 | 2 | 2 | 0 |
| 64 | 2.5 | 2.7 | 2.4 | 2.5 | 2 | 2.1 | 2.2 | 2.1 | 0 |
| 75 | 2 | 2 | 1.8 | 1.9 | 1.2 | 1.6 | 1.5 | 1.4 | 0 |
| 27 | 2.5 | 2.3 | 2.5 | 2.4 | 2 | 2.1 | 2 | 2 | 0 |
| 61 | 1.6 | 2 | 1.5 | 1.7 | 1.8 | 2 | 2 | 1.9 | 0 |
| 22 | 2.2 | 1.7 | 2 | 1.9 | 2 | 2.3 | 2.1 | 2.1 | 0 |
| 18 | 2 | 1.8 | 2 | 1.9 | 2.5 | 2.3 | 2 | 2.2 | 0 |
| 69 | 2.2 | 2 | 2 | 2 | 2.3 | 2.5 | 2.5 | 2.4 | 0 |
| 80 | 2 | 2.1 | 2 | 2 | 2.5 | 2.4 | 2.5 | 2.4 | 0 |

TABLE 4-continued

INHIBITORY EFFECT OF *L. CASEI* OR *L. ACIDOPHILUS*
ON MRSA CLINICAL ISOLATES

| Clinical Isolate # | Inhibition Diameter (cm) | | | | | | | | *Lactococcus* cremoris |
|---|---|---|---|---|---|---|---|---|---|
| | *Lactobacillus acidophilus* I-1492 | | | | *Lactobacillus casei* | | | | |
| | Exp1 | Exp2 | Exp3 | Avg | Exp1 | Exp2 | Exp3 | Avg | |
| 36 | 3 | 3 | 2.9 | 2.9 | 3 | 2.8 | 2.9 | 2.9 | 0 |

No inhibition was detected using *Lactococcus cremoris* thereby showing that not all lactic acid bacteria have growth inhibitory property on methicillin-resistant *Staphylococcus aureus*. The growth inhibition effect was seen using either *Lactobacillus acidophilus* or *Lactobacillus casei* and varied, depending on the MRSA clinical isolate, from 1.7 cm to 2.9 cm for *Lactobacillus acidophilus*, and from 1.4 cm to 2.9 cm for *Lactobacillus casei*. Altogether, this data clearly show the growth inhibitory effect of *Lactobacillus acidophilus* and *Lactobacillus casei* on multiple clinical MRSA isolates.

Example 6

Antibacterial Activities of Mixtures of *L. casei* and *L. acidophilus* on MRSA Clinical Isolate #43

The growth inhibitory effect of mixtures of *Lactobacillus casei* and *Lactobacillus acidophilus* was tested on clinical MRSA isolate #43. The mixtures comprised different concentrations of the two lactobacilli strains as indicated in TABLE 5. Three independent experiments were performed and the average (avg) inhibition diameters in centimeters are shown in TABLE 5. *L. cremoris* was used as a negative control.

TABLE 5

ANTIBACTERIAL ACTIVITIES OF MIXTURES OF *L. CASEI* AND
*L. ACIDOPHILUS* ON MRSA CLINICAL ISOLATE #43

| Strain Ratios L.a.:L.c. | Inhibition Diameter (cm) *Lactobacillus acodophilus* I-1492 (L.a) *Lactobacillus casei* (L.c) | | | | *Lactococcus* cremoris |
|---|---|---|---|---|---|
| | Exp1 | Exp2 | Exp3 | Avg | |
| 2:3 (4 µl L.a.:6 µl L.c) | 2.5 | 3.3 | 3.0 | 2.9 | 0 |
| 4:1 (8 µl L.a.:2 µl L.c.) | 3.0 | 3.5 | 3.3 | 3.2 | 0 |
| 3:2 (6 µl L.a.:4 µl L.c.) | 3.0 | 2.5 | 3.5 | 3.0 | 0 |
| 1:1 (5 µl L.a.:5 µl L.c.) | 3.5 | 3.3 | 3.6 | 3.4 | 0 |
| 1:4 (2 µl L.a.:8 µl L.c.) | 2.6 | 3.0 | 2.7 | 2.7 | 0 |

*3 µl of *L. acidophilus* represents $9 \times 10^6$ cells
*3 µl of *L. casei* represents $5 \times 10^6$ cells.

The inhibition diameters varied from 2.9 cm to 3.4 cm. The ratio that obtained the highest inhibition zone was the 1:1 ratio (volume) wherein the mixture consisted of approximately 64% (of total cells) *L. acidophilus* cells and approximately 36% *L. casei* cells (of total cells). These results clearly show that the relative concentrations of lactic acid bacterial strains in a composition may play a role in favoring maximum inhibition and that the combination of *Lactobacillus casei* and *Lactobacillus acidophilus* is clearly inhibitory to methicillin-resistant *Staphylococcus aureus* growth.

Example 7

Antibacterial Activities of *L. casei* and *L. acidophilus* on Multiple MRSA Clinical Isolates The growth inhibitory effect of *Lactobacillus casei* and *Lactobacillus acidophilus* was tested on a pool of all ten clinical MRSA isolates. Pre-cultures were prepared by incubating *L. acidophilus*, *L. casei* and all MRSA strains for 24 h at 37° C. Antibacterial activity was tested as described above. 3 µl of *L. acidophilus* I-1492 represented $3.8 \times 10^6$ cells, 3 µl of *L. casei* represented $9.6 \times 10^6$ cells and the mixture of both strains represented $6.7 \times 10^6$ cells (3 µl aliquot of a 6 µl mixture). The MRSA isolates were combined by mixing 500 µl of each isolate pre-cultures together, for a total final volume of 5 ml. 200 µl of the 5 ml mix was added to 0.7% BHI-agar added to the lactic bacteria layer (for a total of $1.46 \times 10^7$ cells). The dish was incubated for 24 h at 37° C. and inhibition diameters were measured. *L. cremoris* was used as a negative control whilst MRSA ATCC 43300 served as a positive control. Three independent experiments were performed; the average inhibition diameters in centimeters are shown in TABLE 6.

TABLE 6

ANTIBACTERIAL ACTIVITIES OF *L. CASEI* AND *L. ACIDOPHILUS*
ON MULTIPLE MRSA CLINICAL ISOLATES

| LAB STRAIN(S) | INHIBITION DIAMETER (cm) | | | | | | | |
|---|---|---|---|---|---|---|---|---|
| | MRSA Clinical Isolates (10) | | | | MRSA ATCC 43300 | | | |
| | Exp1 | Exp2 | Exp3 | Avg | Exp1 | Exp2 | Exp3 | Avg |
| *L. casei* + *L. acidophilus* I-1492 1:1 | 3.2 | 3.5 | 3.3 | 3.3 | — | — | — | — |
| *L. acidophilus* I-1492 | 3.0 | 3.2 | 3.0 | 3.0 | 3.0 | 2.6 | 2.7 | 2.7 |
| *L. casei* | 2.2 | 2.5 | 2.3 | 2.3 | 2.0 | 2.5 | 2.4 | 2.3 |
| *Lactococcus cremoris* | 0 | 0 | 0 | 0 | — | — | — | — |

The inhibition diameters varied from 2.3 to 3.3 cm. These results clearly show that lactic acid bacterium strains (alone or in combination) inhibit more than one (multiple) MRSA clinical isolates and that the combination of *Lactobacillus casei* and *Lactobacillus acidophilus* is also inhibitory to multiple clinical methicillin-resistant *Staphylococcus aureus* growth.

Example 8

Antibacterial Activities of BIO-K Plus™ Commercial Preparations on MRSA Clinical Isolate #43

Bio-K Plus™ products are lactic ferment products readily available on the market and sold by the company Bio-K Plus™ International Inc. The antibacterial activity of two Bio-K Plus™ commercial products comprising *L. acidophilus* and *L. casei* was tested. The products were either fermented milk-based or fermented soy-based products. 3 µl of each product was deposited on MRS media and incubated under anaerobic conditions for 24 h at 37° C. (3 µl of milk-based product: $9.9 \times 10^5$ cells; 3 µl of soy-based product: $4.5 \times 10^5$ cells). MRSA #43 was prepared as described above. 200 µl of the MRSA #43 pre-culture was transferred to 7 ml of 0.7% BHI and poured on top of a layer comprising Bio-K Plus™ product bacteria (total MRSA #43: $8.7 \times 10^6$ cells). Three independent experiments were performed and the average inhibition diameters in centimeters are shown in TABLE 7. *L. cremoris* was used as a negative control whilst MRSA ATCC 43300 served as a positive control.

TABLE 7

ANTIBACTERIAL ACTIVITY OF BIO-K PLUS ™ PRODUCTS ON MRSA #43

| Bio-K Plus | INHIBITION DIAMETER (cm) | | | | | | | |
|---|---|---|---|---|---|---|---|---|
| | MRSA #43 | | | | MRSA ATCC 43300 | | | |
| Products | Exp1 | Exp2 | Exp3 | Avg | Exp1 | Exp2 | Exp3 | Avg |
| Milk-based product | 3.2 | 2.9 | 3.0 | 3.0 | 2.8 | 3.0 | 2.7 | 2.8 |
| Soy-based product | 2.5 | 2.3 | 2.5 | 2.4 | 2.0 | 2.3 | 1.8 | 2.0 |
| *Lactococcus cremoris* | 0 | 0 | 0 | 0 | — | — | — | — |

These results show that both products showed inhibitory activity against a clinical MRSA isolate and that the lactic acid bacteria, even in food preparations, inhibit MRSA.

Although the present invention has been described by way of exemplary embodiments, it should be understood by those skilled in the art that the foregoing and various other changes, omissions and additions may be made therein and thereto, without departing from the spirit and scope of the present invention.

REFERENCES

Alvarez-Olmos et al. 2001 Clin Infect Dis. 32(11):1567-76.
D'Souza et al. 2002 BMJ 324(7350):1361.
Jacobsen et al. 1999 Appl Environ Microbiol. 65(11):4949-56.
Lu et al. Am J Clin Nutr. 2001 73(6):1124-1130.
Martins et al. 2007 Microbiology and Immunology Vol. 51 No. 9 pp. 787-795.
Mathur S and Singh R. 2005, Journal of Food Microbiology, 105, 281-295.
Schellenberg et al. 2006 J Microbiol Methods 65(1):1-9.
Shabnam Y., 2002. Characterisation of Methicillin resistant *Staphylococcus aureus* by phenotyping and genotyping method. M.Sc. thesis, Université de Montréal.

The invention claimed is:

1. A method for inhibiting growth of methicillin-resistant *Staphylococcus aureus* bacteria comprising contacting methicillin-resistant *Staphylococcus aureus* bacteria with a composition comprising *Lactobacillus acidophilus* strain I-1492.

2. The method of claim 1, wherein the composition further comprises a strain of *Lactobacillus casei*.

3. The method according to claim 2, wherein the composition comprises about 25% to about 75% of *Lactobacillus acidophilus* strain I-1492.

4. The method according to claim 2, wherein the composition comprises about 33% to about 75% of *Lactobacillus acidophilus* strain I-1492.

5. The method according to claim 2, wherein the composition comprises about 50% to about 75% of *Lactobacillus acidophilus* strain I-1492.

6. The method according to claim 2, wherein the composition comprises about 65% to about 75% of *Lactobacillus acidophilus* strain I-1492.

7. The method according to claim 2, wherein the composition comprises about 75% to about 99% of *Lactobacillus acidophilus* strain I-1492.

* * * * *